United States Patent [19]
Manley

[11] 4,067,328
[45] Jan. 10, 1978

[54] LUNG VENTILATOR

[75] Inventor: Roger Edward Wentworth Manley, Farnham Common, England

[73] Assignee: The Medishield Corporation Limited, London, England

[21] Appl. No.: 708,731

[22] Filed: July 26, 1976

[30] Foreign Application Priority Data

July 29, 1975  United Kingdom ............... 31765/75

[51] Int. Cl.² .......................................... A61M 16/00
[52] U.S. Cl. ............................... 128/145.6; 128/145.7; 128/202
[58] Field of Search ............... 128/145.6, 145.7, 145.8, 128/145.5, 142, 142.2, 142.3, 147, 188, 202, 191 R

[56]  References Cited
  U.S. PATENT DOCUMENTS

| 2,907,322 | 10/1959 | Hay | 128/145.6 |
| 3,754,550 | 8/1973 | Kipling | 128/145.8 |
| 3,842,828 | 10/1974 | Bird | 128/145.8 |
| 3,921,628 | 11/1975 | Smythe et al. | 128/145.6 |

FOREIGN PATENT DOCUMENTS 900,866  7/1962  United Kingdom ............... 128/145.6

Primary Examiner—Ronald L. Frinks
Assistant Examiner—Henry J. Recla
Attorney, Agent, or Firm—Dennison, Dennison, Meserole and Pollack

[57]  ABSTRACT

A lung ventilator which transmits from a bellows respirable gas and/or anaesthetic gas directly to a patient during the inspiratory phase of the patient's breathing cycle and in which, during the expiratory phase of said cycle, the patient exhales directly into a rebreathing bag and at some time during this latter phase, the bellows is caused to inflate to thereby draw in exhaled gas both directly from the patient and from the interior of the rebreathing bag. The bellows and rebreathing bag are isolated one from the other by a biassed flow control valve situated in a conduit linking them together, which valve will allow the contents of the rebreathing bag to be emptied into the patient by squeezing the bag at any time during operation of the ventilator.

4 Claims, 1 Drawing Figure

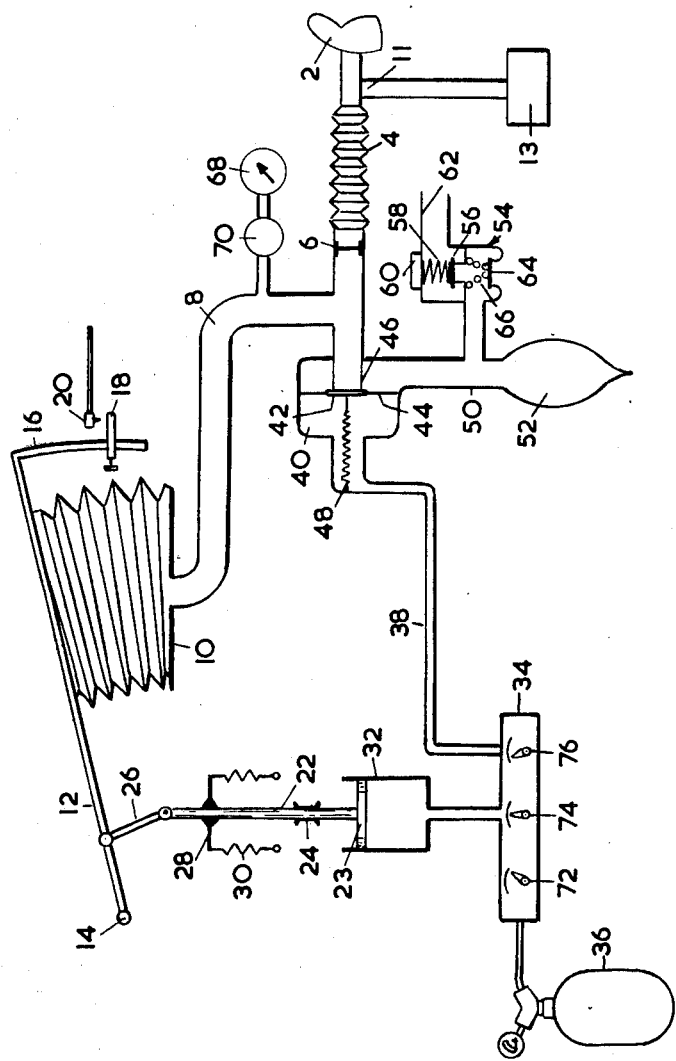

LUNG VENTILATOR

The present invention relates to lung ventilators, particularly for providing constantvolume ventilation for closed circuit anaesthesia.

By 'closed' circuit, constant-volume, ventilation in this specification is meant ventilation in which virtually the same body of gas oscillates between the patient and the ventilator, although normally a small proportion of the gas is vented during each respiratory cycle and is replaced with fresh respirable gas and/or gaseous anaesthetic.

Present day lung ventilators are usually equipped with a rebreathing bag whereby a patient can be ventilated manually by the anaesthetist. The bag is normally cut off from pressurised conduits of the ventilator by a manually-operable valve having one position for automatic ventilation, and another for manual ventilation. This is in convenient in that it requires the anaesthetist to operate the valve before he can ventilate the patient manually. When an emergency occurs, this additional operation of the valve leads to an unwanted delay before the anaesthetist can work the rebreathing bag effectively.

The present invention aims at providing a lung ventilator having a rebreathing bag which is used as a gas accumulator during the expiratory phase of a patient's breathing cycle and is constantly available for manual ventilation irrespective of the instantaneous state of the ventilator.

Accordingly, the present invention provides a "closed circuit" lung ventilator as claimed in any one of the appended claims.

The present invention will now be described by way of example with reference to the accompanying drawing, which is a schema of a lung ventilator of the present invention.

The lung ventilator of the present invention is able to be connected to the breathing passages of a patient by means of a breathing mask 2 or similar device, such as an endotracheal tube. As is conventional, the face mask 2 is connected to the lung ventilator by means of a length of flexible hose 4 which is detachable from a terminal 6 acting as the outlet port of the ventilator. The outlet port is in communication through a large-diameter conduit 8 with the interior of bellows 10. The bellows 10 has one end wall fixed, and has the other end connected to a lever 12 adapted to pivot about a fulcrum 14.

Attached to the outer end of lever 12 is an arcuate scale 16 calibrated over a range of tidal volumes. Moving on scale 16 is a pointer 18 which can be secured to the scale and of which the position determines the particular tidal volume which the bellows 10 can deliver during the inspiratory phase of the respiratory cycle. The pointer 18 is associated with a microswitch 20 which is effective, as discussed below, for signalling the end of the expiratory phase and starting the next inspiratory phase.

The lever 12 is acted on by a pneumatically-operated piston 23 having a piston rod 22 which is engaged by a slide bearing 24 and which is connected to the lever through a pivoted strut 26.

Secured to piston rod 22 is an arm 28 engaged by at least one tension spring 30 which is operable to bias the piston 23 downwardly as viewed.

The piston 23 closes one end of a cylinder 32 which is coupled to one outlet of a flow control block 34. The main inlet of block 34 is coupled to a cylinder 36 or other source of gas at high pressure. The pressure of the gas in the cylinder is reduced to a value of about 276 kNm$^{-2}$ (40 psig), which pressure is able to be introduced into the interior of cylinder 32 at the appropriate phase of the respiratory cycle.

A conduit 38 leads from block 34 to a biassed flow control valve 40 positioned in the patient's exhalation circuit. The valve 40 includes a valve head 42 supported by means of a diaphragm 44. The head 42 is biassed away from an annular valve seat 46 by means of a light tension spring 48. Respired gas which passes between valve head 42 and valve seat 46 flows through a large diameter conduit 50 to the interior of a rebreathing bag 52. Branching from conduit 50 is an auxiliary conduit leading to a combined intake and dump valve 54. The dump valve itself consists of a head 56 adjustably biassed by means of a light compression spring 58 connected to knob 60. The dump valve is surrounded by a shroud 62 which leads to a water or other pump positioned outside the operating theatre so that the atmosphere in the theatre is not polluted by anaesthetic gases dumped from the ventilator.

Valve 54 includes an intake valve head 64 biassed towards a seat by a light spring 66 which is arranged to allow the head 64 to lift, and thereby introduce atmospheric air into the interior of the ventilator, when a pressure of more than 100mm water below atmospheric pressure is produced in the interior of conduit 50.

The pressure in the interior of conduit 8 is indicated by a pressure gauge 68 which is connected to conduit 8 through a bacterial filter 70.

The operation of the illustrated lung ventilator will now be described starting from the beginning of an inspiration phase of the patient's respiratory cycle. At this stage the bellows 10 has been filled via an inlet 11 with gas, preferably with anaesthetic-containing gas, from a supply source 13 to a volume dictated by the setting of pointer 18 on the scale 16. The pressure in cylinder 32 is now released by the expiratory timer (to be described below). Some of the gas thus released from cylinder 32 is vented directly to the atmosphere, but some of it is retained and applied to the interior of conduit 38 to bias the valve head 42 pneumatically into contact with seat 46, being sufficient to overcome the effect of spring 48. This means that all the gas passing down conduit 8 from bellows 10 is forced to flow to the patient.

Gas continues to flow from bellows 10 towards the patient for a time determined by the setting of the inspiratory flow rate control on block 34, which is related to the tidal volume to give the inspiratory time. When this time has elapsed, the block 34 is effective to cause gas under pressure to flow into the interior of cylinder 32 and to vent the interior of conduit 38. The gas pressure supplied to cylinder 32 is sufficient to overcome the bias exerted by tension springs 30. Thus the pressure acts to force the piston rod 22 upwardly (as viewed) to force the lever 12 to move in a direction which inflates bellows 10.

Immediately the gas pressure in conduit 38 was reduced to atmospheric, the spring 48 was able to pull the head 42 away from seat 46. This thus places the patient in direct communication with the rebreathing bag 52 and with the combined intake and dump valve 54. The patient therefore starts to exhale directly to the rebreathing bag, but at some time during this movement of gas the expansion of bellows 10 draws in the exhaled gas both directly from the patient and also from the interior of the rebreathing bag, on a purely arbitrary basis. When the bellows have opened to the desired tidal volume, as indicated by pointer 18 coming into contact with microswitch 20, the bellows cease to move, but usually the patient continues to exhale into the rebreathing bag. This causes the pressure in conduit 50 to rise slowly to a value at which the dump valve 56 opens in order to vent a proportion of the exhaled gases from the interior of the lung ventilator. This loss of gas is normally made up either by fresh atmospheric gas or by a mixture of respirable gas and gaseous anaesthetic supplied as necessary to the interior of conduit 8 from the source of gas supply 13 through inlet 11 by conventional means which are not described in any detail in this specification but which will be known to the man skilled in the art.

The patient is allowed to continue exhaling for a time determined by the setting of another of the three controls projecting from the exterior of block 34.

Control 72 is a simple on/off switch. Control 74 controls the expiratory time, and control 76 controls the inspiratory flow i.e. it determines the rate at which he bellows 10 collapse under the effect of biassing springs 30 to force gas into the patient's lungs.

When the time set by control 74 has elapsed since the beginning of the expiratory phase, the cylinder 32 is depressurised, conduit 38 is pressurised and the breathing cycle as described above is repeated.

It will be seen that, with the illustrated apparatus, the rebreathing bag 52 can be manipulated at any time by the anaesthetist to force gas into the patient, even during the expiratory phase. During the inspiratory phase, i.e. while the bellows 10 are emptying their contents into the patient, the anaesthetist can empty the contents of the rebreathing bag 52 into the patient by squeezing the bag sufficiently hard to raise the pressure in conduit 50 to a value at which the pneumatic bias on valve head 42 is overcome, so that gas from the bag is able to be added to the gas from the bellows. It will thus be seen that the patient can be ventilated manually irrespective of the state of operation of the ventilator.

One of the features of the present invention is that the ventilator is powered solely by the energy contained in the gas cylinder 36. It is this energy which is used to overcome the bias applied by springs 30 in order to operate the bellows, and which is used to overcome the bias of spring 48 so as to control the position of the flow control (or patient) valve 40.

The expiratory time control 74 and the inspiratory flow control 76 are normally formed by adjustable restrictions in the respective gas flow paths. For convenience, these restrictions are preferably formed integrally with the valve block 34, but the block 34 could be replaced by individual components functioning in the same way. The manner in which these controls acts does not form part of the subject-matter of this invention, and so will not be described herein in any further detail.

What is claimed is:

1. A closed-circuit lung ventilator comprising:
   a bellows for delivering respirable gas and/or gaseous anaesthetic to a patient during the inspiratory phase of a patient's breathing cycle and receiving said gas from the patient during the expiratory phase of the patient's breathing cycle:
   inlet means for admitting said gas from a supply therefor to the ventilator;
   a gas port adapted to have attached thereto a breathing mask for delivering said gas to the patient;
   a first conduit connecting said bellows to said gas port;
   a rebreathing bag;
   a second conduit connecting the rebreathing bag to said gas port through said first conduit;
   biased flow control valve means in said second conduit for preventing flow of gas along said first and second conduits from said bellows to said rebreathing bag at controlled time intervals but allowing at all times flow of said gas from said rebreathing bag to said gas port on the manual compression of said rebreathing bag;
   means for establishing controlled time intervals which are a function of the patient's breathing cycle;
   means for forcibly inflating and deflating the bellows at times which are a function of said time intervals;
   means for altering the position of said biased flow control valve as a function of said time intervals so that said valve is open during the expiratory phase of the patient's breathing cycle and closed during the inspiratory phase of the patient's breathing cycle, except when the rebreathing bag has been manually compressed to force the gas therein through the biased flow control valve to the gas port for delivery to the patient;
   the arrangement being such that, in operation of the ventilator, during the inspiratory phase of the patient's breathing cycle the bellows is forcibly deflated to cause a controlled volume of respirable gas and/or gaseous anaesthetic to flow into the patient's lungs while said biased flow control valve is in a position which prevents said gas from flowing from the bellows into the rebreathing bag, and during the expiratory phase of the patient's breathing cycle, the bellows is caused to inflate and take in gas while the biased flow control valve is in a position which allows gas from the patient to be delivered to the bellows and to the rebreathing bag.

2. A lung ventilator as claimed in claim 1, in which the bellows are biassed towards their empty position and are able to be counter-biassed by using a source of gas at high pressure.

3. A lung ventilator as claimed in claim 2, which incorporates means to enable gas released from the counter biasing means to be used to control the position of the said biassed flow-control valve.

4. A ventilator as claimed in claim 2, including a combined intake and dump valve, the dump valve comprising a head adjustably biassed by means of a light compression spring and being surrounded by a shroud which is connectable to a pump positioned remote from the site at which the ventilator is operating so that the atmosphere in the vicinity of said site is not polluted by the anesthetic gases dumped from the ventilator, and the intake valve comprising a valve head biassed towards a seat by a light spring which is arranged to allow the head to lift and thereby introduce atmospheric air into the interior of the ventilator, when the pressure in the interior of the ventilator falls below a chosen value.

* * * * *